(12) United States Patent
Albert et al.

(10) Patent No.: US 7,753,957 B2
(45) Date of Patent: Jul. 13, 2010

(54) BALL AND SOCKET INTERVERTEBRAL DISC REPLACEMENT DEVICE WITH KEYED SURFACES ASSEMBLY

(75) Inventors: Todd James Albert, Narberth, PA (US); Richard H. Rothman, Philadelphia, PA (US); Leon Roitburg, East Hanover, NJ (US); Mikhail Kvitnitsky, Clifton, NJ (US)

(73) Assignee: Accelerated Innovation, LLC, Clifton, NJ (US)

( * ) Notice: Subject to any disclaimer, the term of this patent is extended or adjusted under 35 U.S.C. 154(b) by 27 days.

(21) Appl. No.: 11/376,977

(22) Filed: Mar. 16, 2006

(65) Prior Publication Data

US 2006/0217809 A1     Sep. 28, 2006

Related U.S. Application Data

(60) Provisional application No. 60/665,009, filed on Mar. 24, 2005.

(51) Int. Cl.
  *A61F 2/44* (2006.01)
(52) U.S. Cl. .................. 623/17.14; 623/17.15
(58) Field of Classification Search .............. 623/17.11, 623/17.12, 17.13, 17.14, 17.15, 17.16; 606/61, 606/246, 249; 403/77, 78, 79, 80, 124, 131
See application file for complete search history.

(56) References Cited

U.S. PATENT DOCUMENTS

| | | | | |
|---|---|---|---|---|
| 2,499,030 A | * | 2/1950 | Moon | 464/119 |
| 3,068,032 A | * | 12/1962 | Winsen | 403/78 |
| 3,441,299 A | * | 4/1969 | Pfaar | 403/131 |
| 4,836,485 A | * | 6/1989 | Cooper | 248/278.1 |
| 5,056,951 A | * | 10/1991 | Mariani | 403/90 |
| 5,090,654 A | * | 2/1992 | Ridings et al. | 248/343 |
| 5,246,458 A | | 9/1993 | Graham | |
| 5,480,442 A | | 1/1996 | Bertagnoli | |
| 5,562,737 A | | 10/1996 | Graf | |

(Continued)

OTHER PUBLICATIONS

U.S. Appl. No. 11/488,817, filed Jul. 18, 2006, first named inventor Todd James Albert.

(Continued)

*Primary Examiner*—Eduardo C Robert
*Assistant Examiner*—Jan Christopher Merene
(74) *Attorney, Agent, or Firm*—Matthew B. Dernier, Esq.; Gibson & Dernier LLP (57) ABSTRACT

An intervertebral stabilizer includes: a first plate member operable to engage an endplate of a first vertebral bone of a spine; a second plate member spaced apart from the first plate member and operable to engage an endplate of an adjacent second vertebral bone of the spine; a ball element depending from the first plate member; and a socket element depending from the second plate member, wherein at least one of the ball and socket elements include one or more keyed surfaces such that: (i) an assembly function is obtained in which the ball element may at least one of be received into, and removed from, the socket element in one or more first articulation positions of the first and second plate members; and (ii) a capture function is obtained in which the ball element may at least one of not be received into, and not be removed from, the socket element in one or more second articulation positions of the first and second plate members.

35 Claims, 6 Drawing Sheets

U.S. PATENT DOCUMENTS

| | | |
|---|---|---|
| 5,562,738 A | 10/1996 | Boyd et al. |
| 5,683,465 A | 11/1997 | Shinn et al. |
| 5,989,291 A | 11/1999 | Ralph et al. |
| 6,019,792 A | 2/2000 | Cauthen |
| 6,039,763 A | 3/2000 | Shelokov |
| 6,063,121 A | 5/2000 | Xavier et al. |
| 6,179,874 B1 | 1/2001 | Cauthen |
| 6,228,118 B1 | 5/2001 | Gordon |
| 6,368,350 B1 | 4/2002 | Erickson et al. |
| 6,440,168 B1 | 8/2002 | Cauthen |
| 6,478,822 B1 | 11/2002 | Leroux et al. |
| 6,517,580 B1 | 2/2003 | Ramadan et al. |
| 6,520,996 B1 | 2/2003 | Manasas et al. |
| 6,540,785 B1 | 4/2003 | Gill et al. |
| 6,610,092 B2 | 8/2003 | Ralph et al. |
| 6,616,668 B2 | 9/2003 | Altarac et al. |
| 6,645,248 B2 | 11/2003 | Casutt |
| 6,645,249 B2 | 11/2003 | Ralph et al. |
| 6,669,730 B2 | 12/2003 | Ralph et al. |
| 6,669,731 B2 | 12/2003 | Ralph et al. |
| 6,673,113 B2 | 1/2004 | Ralph et al. |
| 6,679,915 B1 | 1/2004 | Cauthen |
| 6,682,562 B2 | 1/2004 | Viart et al. |
| 6,733,532 B1 | 5/2004 | Gauchet et al. |
| 6,740,117 B2 | 5/2004 | Ralph et al. |
| 6,740,118 B2 | 5/2004 | Eisermann et al. |
| 6,764,515 B2 | 7/2004 | Ralph et al. |
| 6,770,095 B2 | 8/2004 | Grinberg et al. |
| 6,802,867 B2 | 10/2004 | Manasas et al. |
| 6,808,538 B2 | 10/2004 | Paponneau |
| 6,863,688 B2 | 3/2005 | Ralph et al. |
| 6,869,446 B2 | 3/2005 | Ralph et al. |
| 6,994,727 B2 | 2/2006 | Khandkar et al. |
| 7,316,714 B2 * | 1/2008 | Gordon et al. ............ 623/17.16 |
| 2002/0111687 A1 | 8/2002 | Ralph et al. |
| 2003/0014116 A1 | 1/2003 | Ralph et al. |
| 2003/0040802 A1 | 2/2003 | Errico et al. |
| 2003/0065395 A1 | 4/2003 | Ralph et al. |
| 2003/0069642 A1 | 4/2003 | Ralph et al. |
| 2003/0069643 A1 | 4/2003 | Ralph et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0078662 A1 | 4/2003 | Ralph et al. |
| 2003/0216810 A1 | 11/2003 | Ralph et al. |
| 2004/0025464 A1 | 2/2004 | Williams |
| 2004/0034422 A1 | 2/2004 | Errico et al. |
| 2004/0034424 A1 | 2/2004 | Errico et al. |
| 2004/0034425 A1 | 2/2004 | Errico et al. |
| 2004/0034426 A1 | 2/2004 | Errico et al. |
| 2004/0122517 A1 | 6/2004 | Kuras |
| 2004/0225295 A1 | 11/2004 | Zubok et al. |
| 2004/0225365 A1 * | 11/2004 | Eisermann et al. ....... 623/17.15 |
| 2005/0027363 A1 | 2/2005 | Gordon |
| 2005/0033436 A1 | 2/2005 | Schlapfer et al. |
| 2005/0038516 A1 | 2/2005 | Spoonamore |
| 2005/0055029 A1 * | 3/2005 | Marik et al. .................. 606/87 |
| 2005/0060034 A1 | 3/2005 | Berry et al. |
| 2005/0080487 A1 | 4/2005 | Schultz et al. |
| 2005/0080488 A1 | 4/2005 | Schultz |
| 2005/0197703 A1 | 9/2005 | Diaz et al. |
| 2005/0197704 A1 * | 9/2005 | Diaz et al. ................ 623/17.14 |
| 2006/0217809 A1 | 9/2006 | Albert |
| 2007/0073406 A1 * | 3/2007 | Gordon et al. ........... 623/17.15 |
| 2007/0100456 A1 | 5/2007 | Dooris et al. |
| 2007/0150062 A1 * | 6/2007 | Zubok et al. ............. 623/17.14 |
| 2007/0233255 A1 * | 10/2007 | Song et al. ............... 623/17.11 |
| 2008/0065211 A1 * | 3/2008 | Albert et al. ............. 623/17.11 |

OTHER PUBLICATIONS

International Preliminary Report on Patentability for corresponding PCT application PCT/US2006/009663, Mar. 24, 2009.

Office Action for co-pending U.S. Appl. No. 11/488,817, dated Jan. 29, 2010.

Office Action for co-pending U.S. Appl. No. 11/488,817, dated Aug. 6, 2009.

Office Action for co-pending U.S. Appl. No. 11/488,817, dated Feb. 4, 2009.

Office Action for co-pending U.S. Appl. No. 11/488,817, dated Aug. 5, 2008.

* cited by examiner

BALL AND SOCKET INTERVERTEBRAL DISC REPLACEMENT DEVICE WITH KEYED SURFACES ASSEMBLY

CROSS REFERENCE TO RELATED APPLICATIONS

This application claims the benefit of U.S. Provisional Patent Application No. 60/665,009, filed Mar. 24, 2005, the entire disclosure of which is hereby incorporated by reference.

BACKGROUND

The present disclosure generally relates to apparatus and methods for treatment of spinal disorders using an intervertebral prosthesis which is disposed in an intervertebral disc space following removal of a damaged or diseased intervertebral disc.

The bones and connective tissue of an adult human spinal column consists of more than twenty discrete bones coupled sequentially to one another by a tri-joint complex. Each tri-joint complex includes an anterior disc and two posterior facet joints. The anterior discs of adjacent bones are cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine includes the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Conventional intervertebral body cages generally comprise a tubular metal body having an external surface threading. They are inserted transverse to the axis of the spine, into preformed cylindrical holes at the junction of adjacent vertebral bodies. Two cages are generally inserted side by side with the external threading tapping into the lower surface of the vertebral bone above, and the upper surface of the vertebral bone below. The cages include holes through which the adjacent bones are to grow. Additional materials, for example autogenous bone graft materials, may be inserted into the hollow interior of the cage to incite or accelerate the growth of the bone into the cage. End caps are often utilized to hold the bone graft material within the cage.

The cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

An objective in intervertebral disc replacement or intervertebral stabilization is to provide a prosthetic disc that combines both stability to support the high loads of the patient's vertebrae and flexibility to provide the patient with sufficient mobility and proper spinal column load distribution.

Numerous artificial intervertebral discs for replacing a part or all of a removed disc have been developed, namely, elastomer discs, ball and socket discs, mechanical spring discs and hybrid discs. Elastomer discs typically include an elastomer cushion which is sandwiched between lower and upper rigid endplates. The elastomer discs are advantageous in that the elastomer cushion functions similar in mechanical behavior to the removed intervertebral disc tissue. However, a disadvantage of this disc type is that the elastomer cushion experiences long term in-vivo problems stemming from microcracking, which detracts from its usefulness as a replacement option. Furthermore, attachment of the flexible elastomer cushion to rigid endplates presents additional difficulties. Examples of elastomer discs are disclosed in U.S. Pat. Nos. 5,702,450; 5,035,716; 4,874,389; and 4,863,477.

Mechanical spring discs usually incorporate one or more coiled springs disposed between metal endplates. The coiled springs may define a cumulative spring constant sufficient to maintain the spaced arrangement of the adjacent vertebrae and to allow normal movement of the vertebrae during flexion and extension of the spring in any direction. Examples of mechanical spring discs are disclosed in U.S. Pat. Nos. 5,458,642; and 4,309,777.

Ball and socket discs typically incorporate two plate members having cooperating inner ball and socket portions which permit articulating motion of the members during movement of the spine. The ball and socket arrangement is adept in restoring motion of the spine. Examples of ball and socket discs are disclosed in U.S. Pat. Nos. 5,507,816; and 5,258,031. These conventional ball and socket discs include some disadvantageous properties, such as the plate members not remaining interconnected (via the ball and socket) when tensile forces are applied. In other words, the ball is not captured within the socket. While there are existing captured ball and socket discs in the art, they are very complex in the manner in which the ball and socket are interconnected. An example of such a ball and socket configuration is disclosed in U.S. Patent Publication No.: 2003/0069643, the entire disclosure of which is hereby incorporated by reference.

Hybrid artificial intervertebral discs usually incorporate two or more disc types. For example, one known hybrid disc arrangement includes a ball and socket set surrounded by an elastomer ring. This hybrid disc provides several advantages with respect to load carrying ability, but, long term in vivo difficulties with the elastomer cushion remain a concern.

All of the above intervertebral devices suffer from one or more problems, such as being overly complex, difficult to assemble and implant, excessively limit the range of motion of the spine, and/or do not remain assembled in the presence of tensile forces. Thus, there are needs for a new intervertebral stabilizer.

SUMMARY OF THE INVENTION

In accordance with one or more embodiments of the present invention, an intervertebral stabilizer, includes: a first plate member operable to engage an endplate of a first vertebral bone of a spine; a second plate member spaced apart from the first plate member and operable to engage an endplate of an adjacent second vertebral bone of the spine; a ball element depending from the first plate member; and a socket element depending from the second plate member, wherein at least one of the ball and socket elements include one or more keyed surfaces such that: (i) an assembly function is obtained in which the ball element may at least one of be received into, and removed from, the socket element in one or more first articulation positions of the first and second plate members; and (ii) a capture function is obtained in which the ball element may at least one of not be received into, and not be removed from, the socket element in one or more second articulation positions of the first and second plate members.

By way of example, the ball element may define a sphere and the at least one keyed surface thereof may include at least one flat surface interrupting the sphere. The socket element may include an inner surface defining a corresponding sphere and terminating at a peripheral edge such that one or more bisecting-cross sections of the inner surface define arcs of less than or equal to 180 degrees, and one or more other bisecting cross-sections of the inner surface define arcs of greater than 180 degrees. The ball element may define a first axis normal to the at least one flat surface thereof and at least one of the bisecting cross-sections of the inner surface of greater than 180 degrees defines a first plane. The one or more first articulation positions of the first and second plate members may be obtained when the first axis is at least one of substantially parallel to, and co-planar with, the first plane. In contrast, the one or more second articulation positions of the first and second plate members may be obtained when the first axis is at least one of not substantially parallel to, and not co-planar with, the first plane.

An alternative way of describing some aspects of the assembly and capture functions focuses other features of the socket element and the ball element. For example, the socket element may include an inner surface defining a corresponding sphere and terminating at a peripheral edge. One or more portions of the peripheral edge may lay in a plane and one or more other portions of the peripheral edge extend beyond the plane, which one or more other portions define one or more stand offs and one or more corresponding keyed surfaces of the socket element. The one or more first articulation positions of the first and second plate members may be obtained when the at least one flat surface of the ball element is oriented in opposing engagement with the one or more stand offs of the socket element. The one or more first articulation positions permits the at least one flat surface of the ball member to slide relative to the one or more stand offs of the socket element as the ball element is received into, and/or extracted from the socket element.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

It is noted that the numerous figures herein are drawn substantially to scale at least in terms of the relationships among the elements of the particular views shown.

DETAILS OF THE EMBODIMENTS OF THE INVENTION

Figure 1:
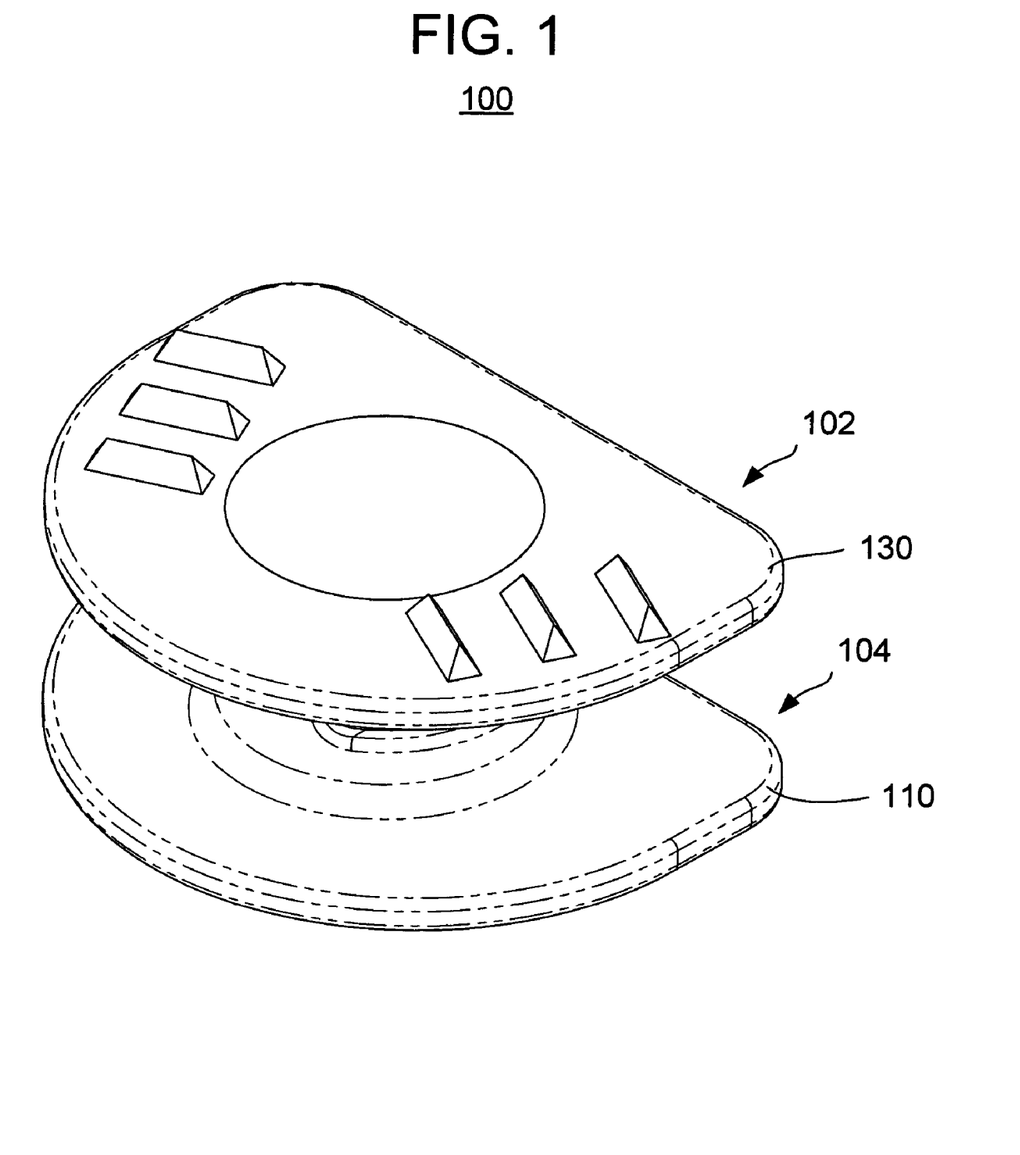
FIG. 1 is a perspective view of an intervertebral disc replacement device in accordance with one or more embodiments of the present invention.
Figure 2:
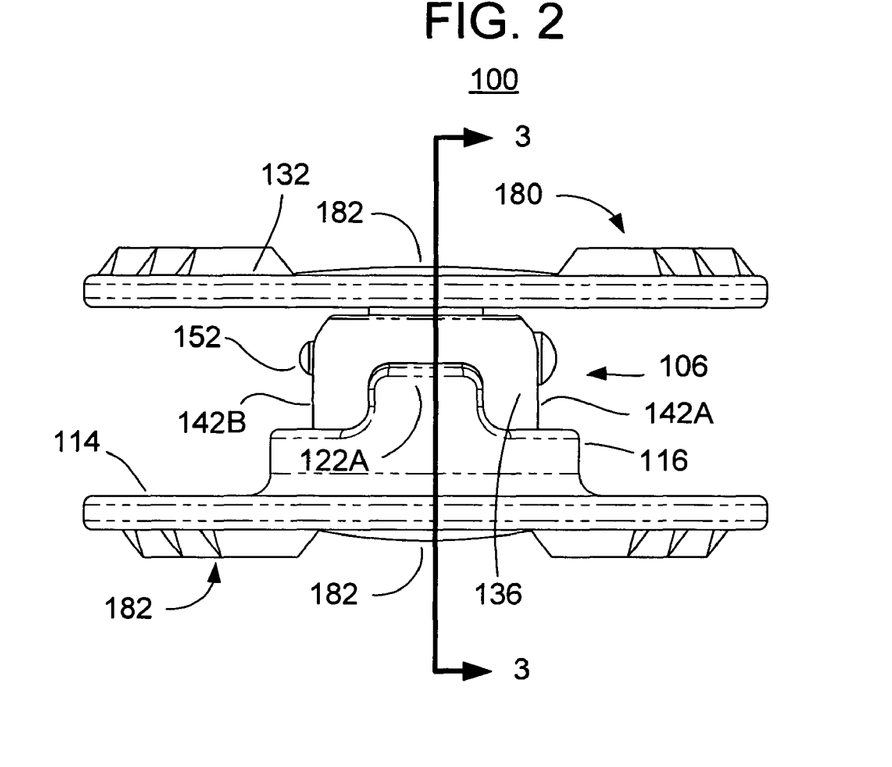
FIG. 2 is a front (anterior) view of the intervertebral disc replacement device of FIG. 1.
Figure 3:
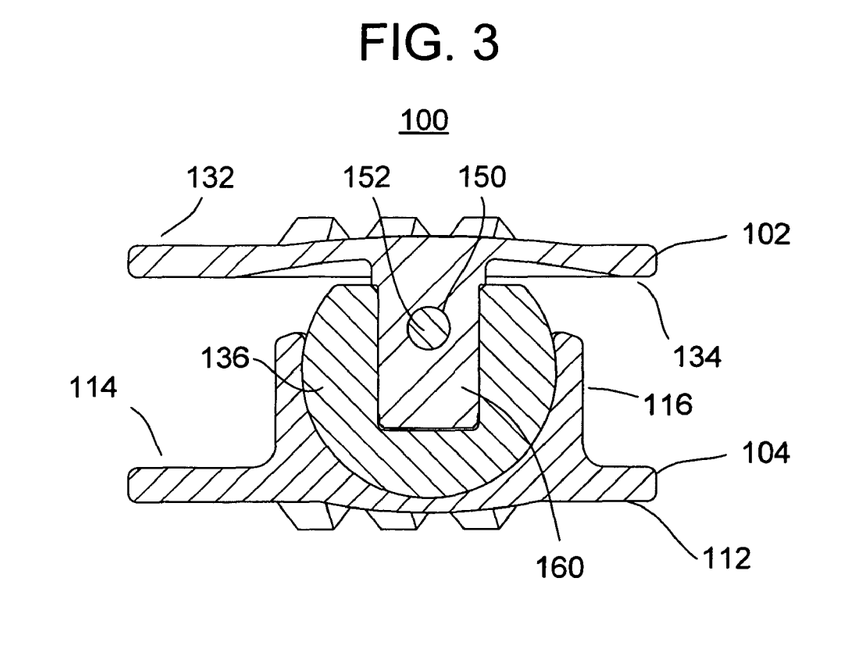
FIG. 3 is a cross-sectional view of the intervertebral disc replacement device of FIG. 2 taken through line 3-3.

Reference is now made to FIGS. 1-3, which illustrate an intervertebral disc replacement device 100 in accordance with one or more embodiments of the present invention. FIG. 1 illustrates a perspective view of the intervertebral disc replacement device 100, while FIG. 2 is a front (anterior) view of the device 100. FIG. 3 is a cross-sectional view of the intervertebral disc replacement device 100 taken through line 3-3 (as shown in FIG. 2). The device 100 generally includes two plate members 102, 104 that are coupled together by way of a ball and socket assembly 106. The intervertebral disc replacement device 100 is sized and shaped to fit in the intervertebral space between adjacent vertebral bones of the spine. It is understood that the size and shape of the intervertebral disc replacement device 100 may be adapted to fit in an intervertebral space at any level of the spine, such as the cervical spine, thoracic spine, or lumbar spine. The intervertebral disc replacement device 100 is sized and shaped to be inserted into the inter-vertebral space from an anterior direction.

The plate member 104 includes a plate 110 of substantially planar configuration, which includes an engagement surface 112 spaced apart from an opposing surface 114. The engagement surface 112 is preferably operable to couple with an end plate of a vertebrae from which an associated disc has been removed. The plate member 102 preferably includes a plate 130 of substantially planar configuration having an engagement surface 132 and a spaced apart opposing surface 134. Preferably, the peripheral shape of the plates 110 and 130 are of a complimentary nature with respect to the shape of the corresponding end-plates of the vertebrae. While the engagement surfaces 112, 132 may be substantially flat, such may alternatively include one or more bone adhesion facilitating elements 180, which are operable to promote bone adhesion to the vertebral bones. For example, the bone adhesion facilitating elements 180 may include one or more of spikes, one or more keels, one or more roughening elements, and the like. In addition, numerous other modifications may be employed on the plates 110, 130, such as angulation elements in any or numerous directions, screws, flanges, coatings, dimples, beads, shock absorption members, etc. One or more of the engagement surfaces 112, 132 may also include a domed portion 182 that is sized and shaped to correspond to the concave shape of the endplates of the vertebral bones.

The ball and socket assembly 106 may include a socket element 116 extending from the opposing surface 114 of the plate 110 in a transverse direction, preferably perpendicular thereto. The ball and socket assembly 106 may also include a ball element 136 extending from the opposing surface 134 of the plate 130, preferably in a transverse direction (e.g., perpendicular). The ball and socket assembly 106 is operable such that the ball element 136 may be received into, and removed from, the socket element 116 in one or more first articulation positions of the plate members 102, 104. Once received into the socket element 116, the ball element 136 may not be removed when the plate members 102, 104 are in one or more second articulation positions. In this regard, the phrase "articulation position" is intended to include within its meaning: articulation (such as orientations of the plates that would result from anterior-posterior flexing and lateral bending of the vertebral bones), rotation, translation, and/or any combination of the above motions/orientations of the plate members 102, 104. Also, the word "articulation" is intended to include within its meaning: articulation (such as orientations of the plates that would result from anterior-posterior flexing and lateral bending of the vertebral bones), rotation, translation, and/or any combination of the above motions.

Figure 4:
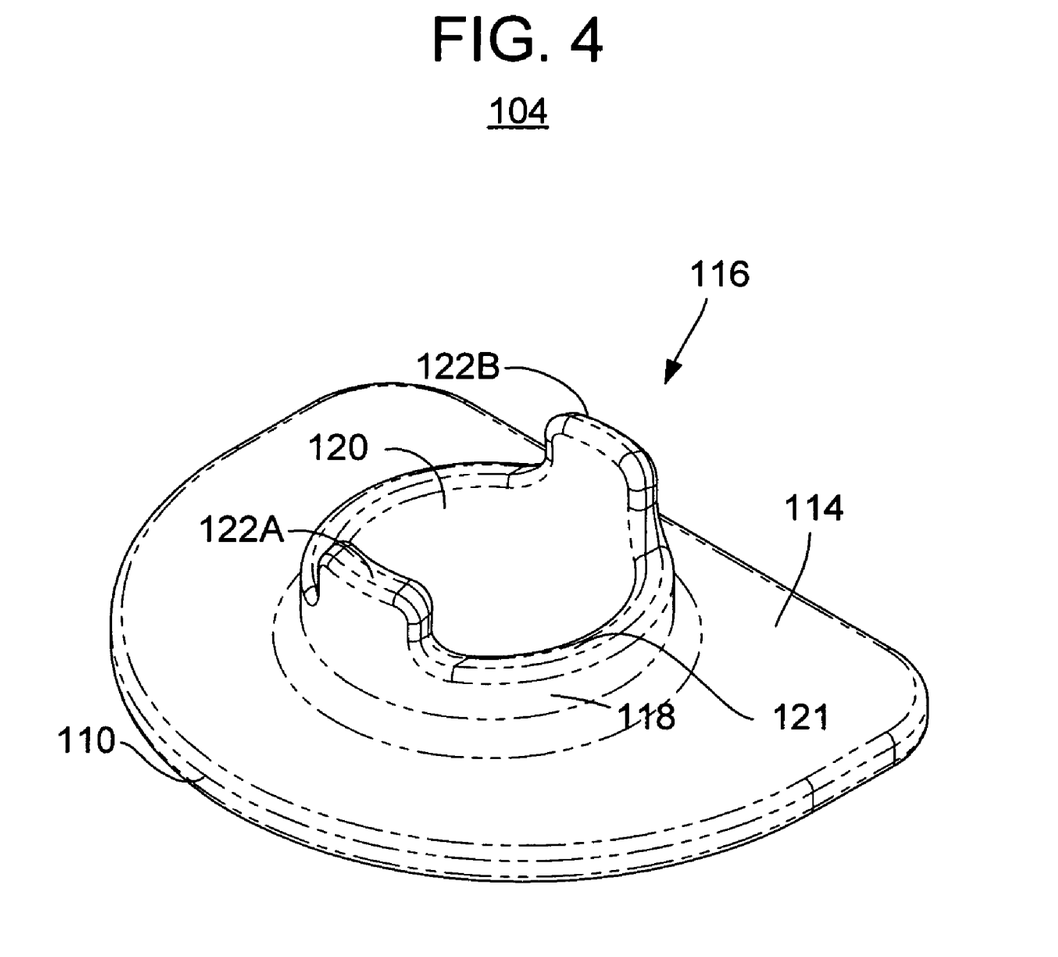
FIG. 4 is a perspective view of a plate member of the intervertebral disc replacement device of FIG. 1.
Figure 5:
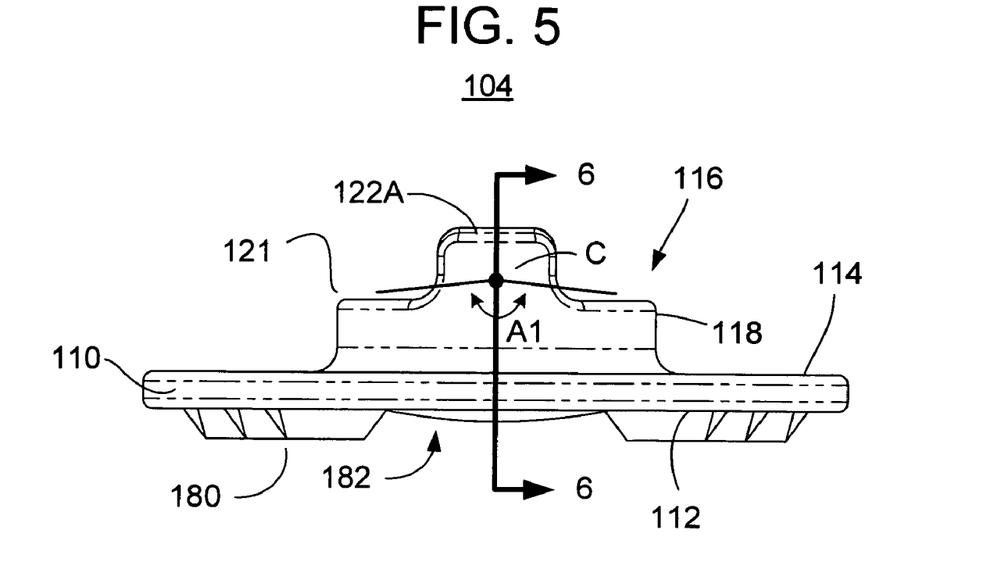
FIG. 5 is a front (anterior) view of the plate member of FIG. 4.
Figure 6:
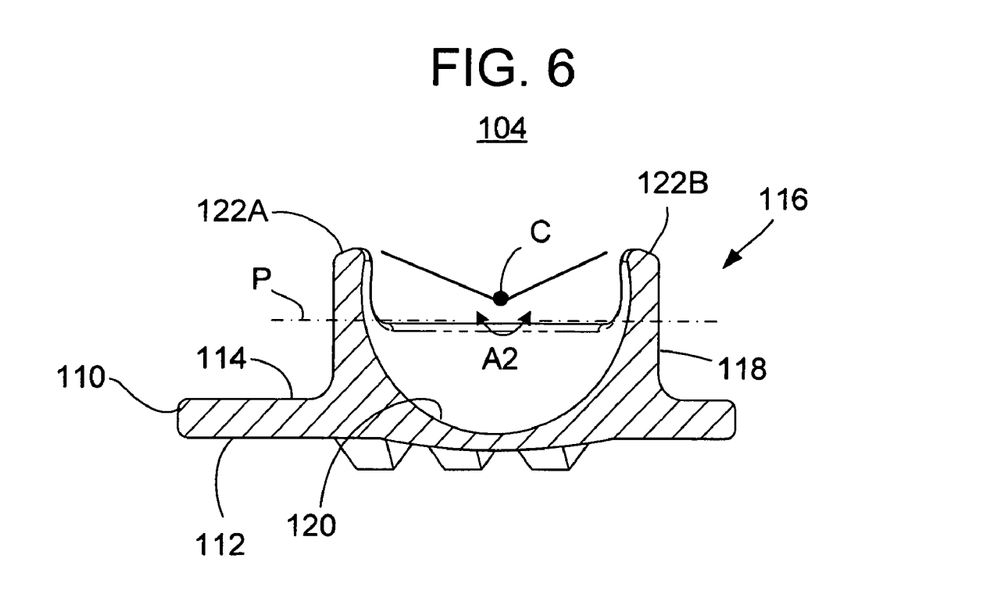
FIG. 6 is a cross-sectional view of the plate member of FIG. 5 taken through line 6-6.

With reference to FIGS. 4-6, further details regarding the plate member 104 will now be provided. FIG. 4 is a perspective view of the plate member 104, while FIG. 5 is a front (anterior) view thereof. FIG. 6 is a cross-sectional view of the plate member 104 taken through line 6-6 (as shown in FIG. 5). The socket element 116 includes an annular wall 118 defining an interior surface 120, wherein the interior surface 120 is of a size and shape to permit articulation of the ball element 136 therein.

Figure 7:
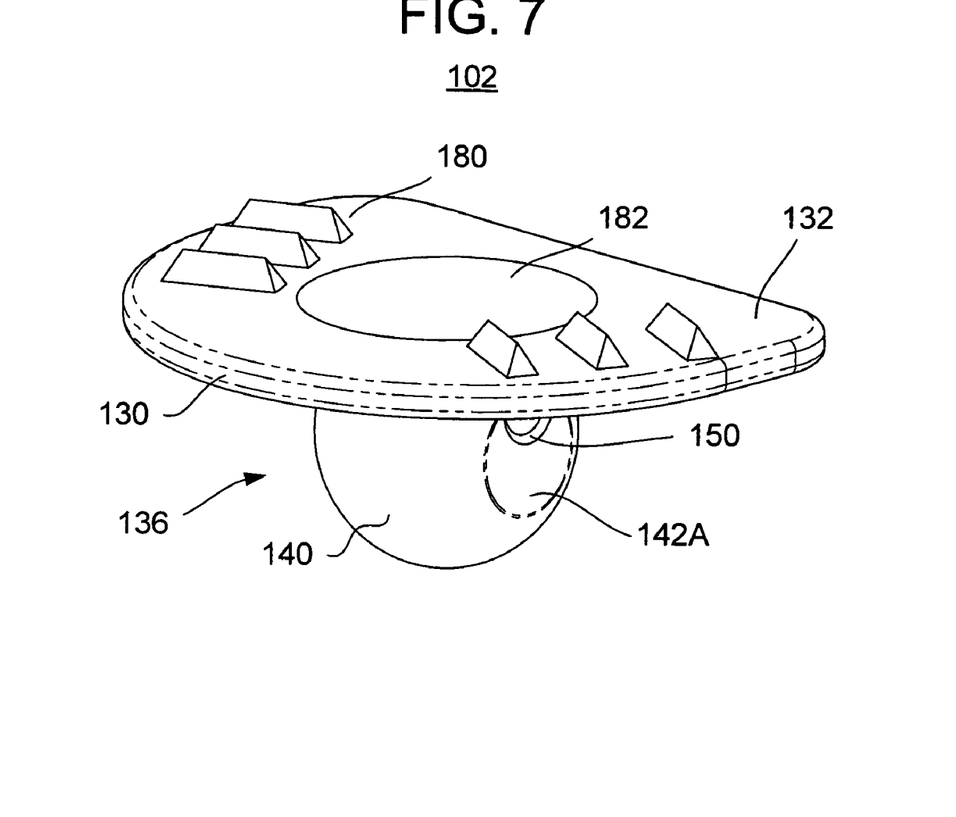
FIG. 7 is a perspective view of another plate member of the intervertebral disc replacement device of FIG. 1.
Figure 8:
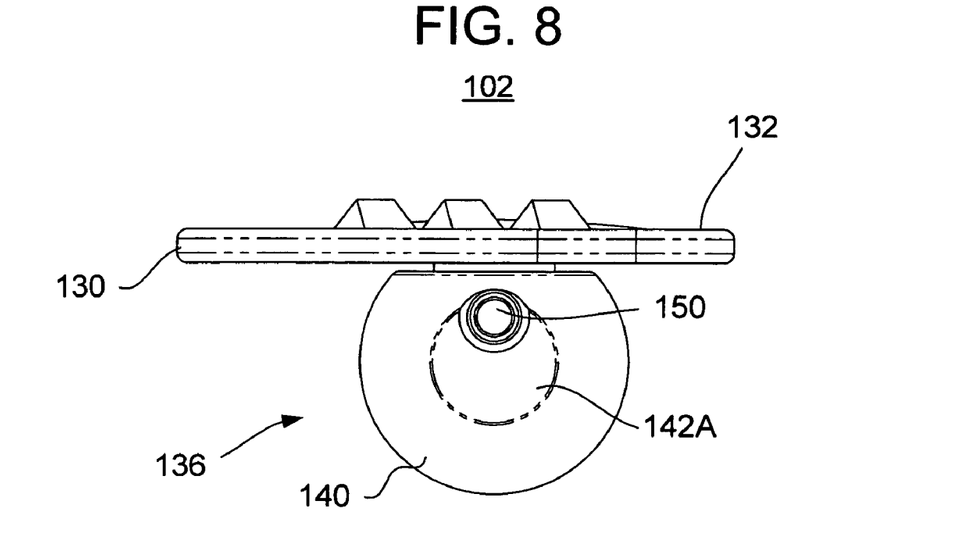
FIG. 8 is a side (lateral) view of the plate member of FIG. 7.
Figure 9:
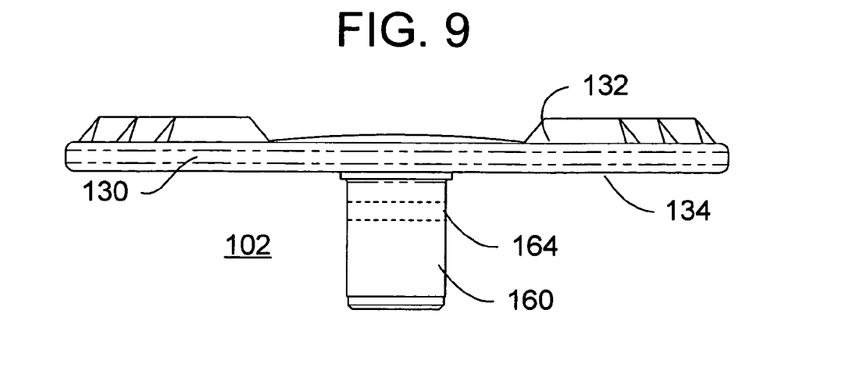
FIG. 9 is a front (anterior) view of an embodiment of the plate member of FIG. 7.

With reference to FIGS. 7-8, which illustrate views of the plate member 102, the ball element 136 includes an outer surface 140 having a first contour. The interior surface 120 of the socket member 116 has a second contour defining a volume. The first and second contours preferably complement one another such that the ball element 116 may articulate within the volume of the socket element 116. For example, the interior surface 120 of the socket element 116 and the outer surface 140 of the ball element 136 may define respective, substantially spherical configurations. It is noted, however, that the interior surface 120 of the socket element 116 need not define a complete sphere, but rather a partial sphere having an edge that terminates along a peripheral edge 121 of the annular wall 118.

At least a portion of the peripheral edge 121 of the inner surface 120 of the socket element 116 may define a profile that, together with the first contour of the ball element 136, achieves the aforementioned assembly and capture functions—that the ball element 136 may be received into, and removed from, the socket element 116 in one or more first articulation positions of the plate members 102, 104, but once received into the socket element 116, the ball element 136 may not be removed when the plate members 102, 104 are in one or more second articulation positions. For example, when the plate member 102 is in the orientation illustrated in FIG. 8 and the plate member 104 is in the orientation illustrated in FIG. 5, the ball element 136 may be received into, and removed from, the socket element 116—they may be assembled. On the other hand, once assembled, as in FIG. 3, the plate members 102, 104 are in different relative orientations and the ball element 136 may not be removed from the socket element 116—the ball element 136 is captured within the socket element 116.

In one or more embodiments, one or both of the ball element 136 and the socket element 116 may include keyed surfaces or keyed portions that operate together to achieve the assembly and/or capture functions. For example, the first contour of the outer surface 140 of the ball element 136 may include one or more keyed surfaces, such as one or more flat portions 142 (two such flat portions 142A, 142B being shown by way of example—although any number may be employed). Additionally, the profile of the peripheral edge 121 of the inner surface 120 of the socket element 116 may include at least one corresponding keyed portion. By way of example, the annular wall 118 may include one or more stand-offs 122 (two such stand-offs 122A, 122B being shown by way of example—although any number may be employed). While some portions of the peripheral edge 121 lay in a plane P (see FIG. 6), the portions of the peripheral edge 121 at the stand-offs 122A, 122B, extend beyond the plane P. The assembly function is permitted only when the keyed surfaces (flat portions) 142A, 142B of the ball element 136 are positioned in sliding relation to the corresponding keyed portions (stand-offs 122A, 122B) of the socket element 116. In particular, this orientation of the plate members 102, 104 permits the flat portions 142A, 142B of the ball member 136 to slide relative to the one or more stand-offs 122A, 122B of the socket element 116 as the ball element 136 is received into, and/or extracted from the socket element 116.

The one or more flat portions 142 interrupt the spherical shape of the ball element 136, reducing a diameter of the ball element 136 in at least one axis. Preferably, the size and position of the one or more flat portions 142 are such that they compliment the positions of the stand-offs 122 of the socket 116 and permit the ball element 136 to slide past the stand-offs 122 and into the socket element 116 when in the correct orientation(s). In the illustrated example, the ball member 136 includes two flat portions 142A, 142B that are disposed substantially opposite to one another and in a configuration that is rotationally offset from the positions of the stand-offs 122A, 122B. In other words, the two flat portions 142A, 142B define an axis (passing therethrough) that is rotationally offset from and axis passing through the stand-offs 122A, 122B. This rotational offset is best seen in FIGS. 1-3, where the axes would be transverse to one another.

Thus, to couple the plate members 102, 104 together, the plate members 102, 104 are preferably rotated (e.g., 90 degrees) with respect to one another (see FIGS. 5 and 8) and the ball element 136 is inserted into the socket element 116 such that the flat portions 142A, 142B pass in an abutted relationship to the stand-offs 122A, 122B. The surface 140 of the ball 136 eventually engages the interior surface 120 of the socket 116. Then, the plate members 102, 104 may be rotated with respect to one another such that the flat portions 142A, 142B are not in abutted relationship with the stand-offs 122A, 122B and the ball element 136 is captured within the socket element 116. Once the ball element 136 is captured within the socket element 116, and implanted in a intervertebral disc space of a patient, the one or more articulation positions that permit assembly/disassembly are at least unlikely to be repeated—and are preferably impossible to repeat.

As best seen in FIGS. 5-6, the assembly and capture of the ball element 136 in the socket element 116 are achieved by way of the differing curvature features provided by the contour of the interior surface 120 and peripheral edge 121 thereof. For example, one or more bisecting-cross sections of the inner surface 120 define arcs (e.g., arc A1 in FIG. 5) of less than or equal to 180 degrees, while one or more other bisecting cross-sections of the inner surface 120 define arcs (e.g. arc A2 in FIG. 6) of greater than 180 degrees. The contour of the interior surface 120 (and the peripheral edge 121 thereof) cannot capture the ball element 136 when the bisecting-cross section(s) of the inner surface 120 defines and arc (or arcs) of less than or equal to 180 degrees. At the stand-offs 122A, 122B, however, the contour of the interior surface 120 (and the peripheral edge 121 thereof) can capture the ball element 136 because the bisecting-cross section(s) of the inner surface 120 there define arcs of greater than 180 degrees. The diameter of the opening (or profile) into the socket element 116 at the stand-offs 122A, 122B is smaller than the maximum diameter of the inner surface 120 generally, and smaller than the diameter across other portions of the peripheral edge 121. Owing to the corresponding smaller diameter of the ball element 136 through the flat portions 142A, 142B, the ball member 136 may clear the peripheral edge 121 of the socket element 116 when the flat portions 142A, 142B are aligned with the stand-offs 122A, 122B. (It is noted that this alignment may happen when an axis normal to the flat surface(s) 142 is substantially parallel to and/or co-planar with a plane defined by one of the bisecting cross-sections of the inner surface 120 of greater than 180 degrees.

Once captured, the ball element 136 and the socket element 116 are sized and shaped such that the plate members 102, 104 may achieve various rotational positions without losing the capture of the ball element 136 within the socket element 116. Indeed, in these rotational positions, the plate members 102, 104 may experience tensile forces without separating because the ball element 136 is captured within the socket element 116. When the amount of rotation of the first and second members 102, 104 is such that the flat portions 142 abut the stand-offs 122, however, the plate members 102, 104 cannot withstand tensile forces and may separate (e.g., the ball element 136 may exit from the socket element 116). Further, the spherical nature of the socket element 116 and the ball element 136 is such that numerous and various articulations may be achieved with respect to the plate members 102, 104. Thus, when the device 100 is inserted between vertebrae (and are attached thereto) the device 100 may aid in the articulation between the vertebrae.

With reference to FIGS. 2, 3, and 8, in one or more alternative embodiments, the ball element 136 may include an aperture 150 extending through at least one flat portion 142, such as from one flat portion 142A to the other flat portion 142B. The aperture 150 may accommodate the insertion of a pin 152 (FIG. 12), which pin 152 may prevent rotation of the plate members 102, 104 with respect to one another beyond a predetermined articulation positions, thereby insuring the ball element 136 remains captured within the socket element 116. In other words, the pin 152 may be operatively connectable to the ball element 136 via the aperture 150 after insertion into the socket element 116 such that the pin 152 is operable to prevent the plate members 102, 104 from obtaining the one or more first articulation positions. At the predetermined articulation positions, the pin 152 engages one or more structures of the socket element 116, such as the stand-offs 122A, 122B. It is noted that the limit in articulation as between the plate members 102, 104 may be a desirable feature, as the articulation between adjacent vertebral bones of a healthy spine is limited by various anatomical structures (such as facets, ligaments, etc.) The degree to which the articulation of the plate members 102, 104 is limited may be adjusted by the placement of the keyed surfaces of the socket element 116 with respect to the pin 152. In the illustrated embodiment (see FIGS. 2-3), the angular positions of the pin 152 with respect to the stand-offs 122A, 122B determines the permissible articulation of the plate members 102, 104.

Figure 10:
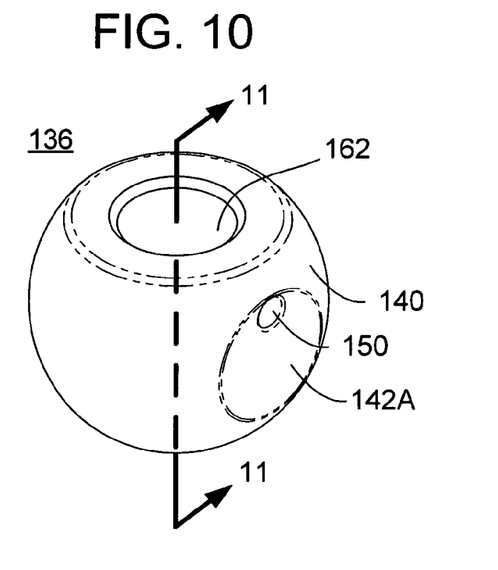
FIG. 10 is a perspective view of a ball member of an embodiment of the plate member of FIG. 7.
Figure 11:
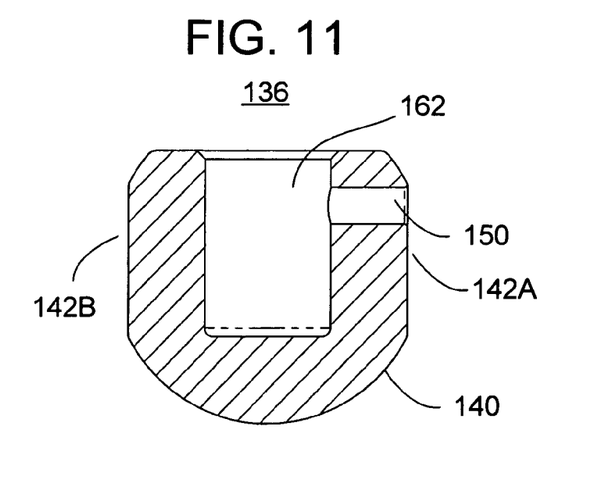
FIG. 11 is a cross-sectional view of the ball member of FIG. 10 taken through line 11-11.
Figure 12:
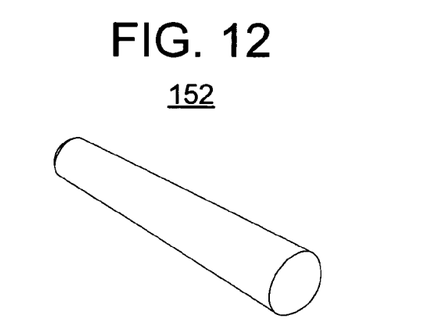
FIG. 12 is a perspective view of a pin for locking the elements of the intervertebral disc replacement device together.

With reference to FIGS. 10-11 (FIG. 11 being a cross-sectional view of FIG. 10 taken through line 11-11), in one or more alternative embodiments, the plate member 102 may include a shaft 160 extending transversely from the opposing surface 134. The ball element 136 may include a bore 162 sized and shaped to receive the shaft 160, thereby coupling the ball element 136 to the plate member 102. The shaft 160 and bore 162 may be fixed to one another via any suitable means, such as adhesives, fusion, shrink fit (temperature, interference fit), etc. Alternatively, the shaft 160 may include a bore 164 that may be placed in registration with the aperture 150 of the ball element 136. The pin 152 may be sized and shaped to engage the respective bores 150, 164 to fix the ball element 136 to the shaft 160. The pin 152 may perform another function, as discussed above, which is to prevent the plate members 102, 104 from obtaining the one or more first articulation positions, thereby capturing the ball element 136 within the socket element 116. As illustrated in FIG. 12, the pin 152 may include at least a conically shaped portion.

Advantageously, the substantially two-piece construction of the device 100 permits a surgeon to select, mix, and match the plate members 102, 104 during surgery. This may accommodate the particular anatomy of the patient such as differing sized vertebrae, etc., which may best be evaluated during surgery. Moreover, once the surgeon has selected the plate members 102, 104, they may be easily coupled together and implanted as one piece.

Some notable features of the aforementioned device 100 are listed below, it being understood that various features alone or in combination may be employed: 1) The device is of a substantially two-piece construction but achieves a one-piece implantation; 2) The device may be pre-assembled prior to surgery or may be delivered for surgery in modular form for assembly during surgery; 3) The modularity permits interoperative selection of sizes, end plate angulations, fastening means, etc.; and 4) The device exhibits simple assembly and locking.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intervertebral disc replacement device, comprising:
   a first plate member operable to engage an endplate of a first vertebral bone of a spine;

a second plate member spaced apart from the first plate member and operable to engage an endplate of an adjacent second vertebral bone of the spine;

a ball element depending from the first plate member; and a one-piece socket element depending from the second plate member, wherein:

at least one of the ball and one-piece socket elements include one or more keyed surfaces such that: (i) the ball element is at least one of received into and removed from the one-piece socket element in one or more first articulation positions of the first and second plate members; and (ii) the ball element cannot be at least one of received into and removed from the one-piece socket element in one or more second articulation positions of the first and second plate members, the one piece socket element comprises an inner surface defining a recess sized and shaped to receive a substantial portion of the ball element and terminating at a peripheral edge such that one or more portions of the peripheral edge define one or more stand offs that extend longitudinally away from the recess and beyond a transverse plane comprising the peripheral edge, and the one or more stand offs respectively form the one or more keyed surfaces for the one-piece socket element.

2. The intervertebral disc replacement device of claim 1, wherein the one or more first articulation positions are at least unlikely to be repeated after the intervertebral disc replacement device has been implanted in a patient.

3. The intervertebral disc replacement device of claim 1, wherein the one or more first articulation positions are not repeatable after the intervertebral disc replacement device has been implanted in a patient.

4. The intervertebral disc replacement device of claim 1, wherein:

the ball element includes an outer surface having a first contour; and the one-piece socket element includes an inner surface having a second contour defining a volume, the first and second contours complementing one another such that the ball element may articulate within the volume of the socket.

5. The intervertebral disc replacement device of claim 4, wherein at least a portion of a peripheral edge of the inner surface of the one-piece socket element defines a profile, together with the first contour of the ball element, such that the ball element is at least one of received into and removed from the one-piece socket element in one or more first articulation positions of the first and second plate members; and the ball element cannot be at least one of received into and removed from the one-piece socket element in one or more second articulation positions of the first and second plate members.

6. The intervertebral disc replacement device of claim 5, wherein:

the first contour of the ball element includes at least one keyed surface and the at least one keyed surface cooperates with the stand offs such that the ball element is at least one of received into and removed from the one-piece socket element in the one or more first articulation positions of the first and second plate members; and the ball element cannot be at least one of received into and removed from the one-piece socket element in the one or more second articulation positions of the first and second plate members.

7. The intervertebral disc replacement device of claim 6, wherein:

the first contour of the ball element defines a sphere and the at least one keyed surface thereof interrupts the sphere;

the second contour of the one-piece socket element defines a corresponding sphere;

the ball element is permitted to be at least one of received into and removed from the one-piece socket element in one or more first articulation positions of the first and second plate members only when the at least one keyed surface of the ball element is substantially aligned with, and positioned in sliding relation to, the at least one corresponding keyed portion of the one-piece socket element; and the ball element cannot be at least one of received into and removed from the one-piece socket element in one or more second articulation positions of the first and second plate members only when the at least one keyed surface of the ball element is not substantially aligned with, and not positioned in sliding relation to, the at least one corresponding keyed portion of the one-piece socket element.

8. The intervertebral disc replacement device of claim 1, wherein the ball element defines a sphere and the at least one keyed surface thereof includes at least one flat surface interrupting the sphere.

9. The intervertebral disc replacement device of claim 8, wherein the one-piece socket element includes an inner surface defining a corresponding sphere and terminating at the peripheral edge such that one or more bisecting-cross sections of the inner surface define arcs of less than or equal to 180 degrees, and one or more other bisecting cross-sections of the inner surface define arcs of greater than 180 degrees.

10. The intervertebral disc replacement device of claim 9, wherein:

the ball element defines a first axis normal to the at least one flat surface thereof;

at least one of the bisecting cross-sections of the inner surface of greater than 180degrees defines a first plane; and the one or more first articulation positions of the first and second plate members is obtained when the first axis is at least one of substantially parallel to, and co-planar with, the first plane.

11. The intervertebral disc replacement device of claim 10, wherein the one or more second articulation positions of the first and second plate members is obtained when the first axis is at least one of not substantially parallel to, and not co-planar with, the first plane.

12. The intervertebral disc replacement device of claim 1, wherein the one or more first articulation positions of the first and second plate members is obtained when the at least one flat surface of the ball element is oriented in opposing engagement with the one or more stand offs of the one-piece socket element.

13. The intervertebral disc replacement device of claim 12, wherein the one or more first articulation positions permits the at least one flat surface of the ball member to slide relative to the one or more stand offs of the one-piece socket element as the ball element is received into, and/or extracted from the one-piece socket element.

14. The intervertebral disc replacement device of claim 1, wherein:

the one-piece socket element includes a plurality of stand offs and the ball element includes a corresponding plurality of flat surfaces; and the one or more first articulation positions of the first and second plate members is obtained when the flat surfaces of the ball element are each oriented in opposing engagement with corresponding ones of the stand offs of the one-piece socket element.

15. The intervertebral disc replacement device of claim 1, wherein:
one or more bisecting-cross sections of the inner surface that do not include at least one stand off define arcs of less than or equal to 180 degrees; and
one or more other bisecting cross-sections of the inner surface that include at least one stand off define arcs of greater than 180 degrees.

16. The intervertebral disc replacement device of claim 1, further comprising a pin element operatively connectable to the ball element after insertion into the one-piece socket element, the pin element being operable to prevent the first and second plate members from obtaining the one or more first articulation positions, thereby capturing the ball element within the one-piece socket element.

17. The intervertebral disc replacement device of claim 1, further comprising one or more bone adhesion facilitating elements disposed on at least one of the first and second plate members, and operable to promote bone adhesion to at least one of the first and second vertebral bones.

18. The intervertebral disc replacement device of claim 17, wherein the one or more bone adhesion facilitating elements includes at least one of:
one or more spikes extending from at least one of the first and second plate members for promoting engagement thereof with the associated vertebral bones;
one or more keels extending from at least one of the first and second plate members for promoting engagement thereof with the associated vertebral bones; and
one or more roughening elements one at least one of the first and second plate members for promoting engagement thereof with the associated vertebral bones.

19. An intervertebral disc replacement device, comprising:
a first plate member operable to engage an endplate of a first vertebral bone of a spine, the first plate member including a shaft extending transversely therefrom;
a second plate member operable to engage an endplate of an adjacent second vertebral bone of the spine, the second plate member including a socket element; and
a ball element including a bore sized and shaped to receive the shaft, thereby coupling the ball element to the first plate member, wherein:
at least one of the ball and socket elements include one or more keyed surfaces such that: (i) the ball element operates to be received into the socket element only in two or less first articulation positions of the first and second plate members; and (ii) the ball element operates to not be removed from the socket element in one or more second articulation positions of the first and second plate members, and
the socket element comprises a recess shaped to receive a substantial portion of the ball element, the recess terminating at a peripheral edge lying in a plane such that one or more portions of the peripheral edge extend vertically beyond the plane and outside the recess, such that the one or more portions respectively define one or more stand offs forming the one or more keyed surfaces for the socket element.

20. The intervertebral disc replacement device of claim 19, wherein the shaft includes a respective bore, the ball element includes a respective bore, and the respective bore of the shaft and the respective bore of the ball element are placed in registration with one another.

21. The intervertebral disc replacement device of claim 20, further comprising a pin element that is sized and shaped to engage the respective bores to fix the ball element to the shaft.

22. The intervertebral disc replacement device of claim 20, further comprising a pin element that is sized and shaped to engage the respective bores such that after insertion into the socket element, the pin element is operable to prevent the first and second plate members from obtaining the two or less first articulation positions, thereby capturing the ball element within the socket element.

23. The intervertebral disc replacement device of claim 22, wherein the pin element includes at least a conically shaped portion.

24. An intervertebral disc replacement device, comprising:
a first plate member operable to engage an endplate of a first vertebral bone of a spine, and including a ball element extending transversely therefrom;
a second plate member spaced apart from the first plate member, operable to engage an endplate of an adjacent second vertebral bone of the spine, and including a socket element depending therefrom; and
at least one of the ball and socket elements include one or more keyed surfaces that provide a locking mechanism operable such that: (i) the ball element is operable to be received into the socket element only in one or more first articulation positions of the first and second plate members; and (ii) the ball element is operable to not be removed from the socket element in one or more second articulation positions of the first and second plate members,
wherein the socket element comprises an inner surface defining a recess shaped to accommodate a substantial portion of the ball element and terminating at a peripheral edge wherein one or more portions of the peripheral edge extend longitudinally outside the recess beyond a transverse plane comprising the peripheral edge, such that the one or more portions respectively define one or more stand offs forming the one or more keyed surfaces for the socket element.

25. The intervertebral disc replacement device of claim 24, wherein the locking mechanism is further operable to prevent rotation of the first and second plate members with respect to one another beyond a predetermined angle.

26. The intervertebral disc replacement device of claim 25, wherein the locking mechanism includes a locking element operatively connectable to the ball element after insertion into the socket element, the locking element being operable to prevent the first and second plate members from obtaining the two or less first articulation positions, thereby capturing the ball element within the socket element.

27. The intervertebral disc replacement device of claim 24, wherein:
the first plate member includes a shaft extending transversely therefrom;
the ball element includes a bore sized and shaped to receive the shaft, thereby coupling the ball element to the first plate member; and
the locking mechanism is further operable to prevent the ball element from disengaging from the shaft.

28. The intervertebral disc replacement device of claim 27, wherein the locking mechanism includes:
a respective bore in the shaft that is placed in registration with a respective bore in the ball element; and
a locking element that is sized and shaped to engage the respective bores of the shaft and the ball element to fix the ball element to the shaft.

29. The intervertebral disc replacement device of claim 28, wherein the locking element includes a pin element that is sized and shaped to engage the respective bores.

30. The intervertebral disc replacement device of claim 29, wherein the pin element includes at least a conically shaped portion.

31. A method of assembling an intervertebral disc replacement device, comprising:

providing a first plate member operable to engage an endplate of a first vertebral bone of a spine, and including a ball element extending transversely therefrom;

providing a second plate member spaced apart from the first plate member, operable to engage an endplate of an adjacent second vertebral bone of the spine, and including a socket element depending therefrom;

providing at least one of the ball and the one-piece socket elements with one or more keyed surfaces such that: (i) the ball element may be received into the socket element only in the one or more first articulation positions of the first and second plate members and (ii) the ball element may not be removed from the socket element in one or more second articulation positions of the first and second plate members;

orienting the first and second plate members in the first articulation position;

inserting the ball element into the socket element while maintaining the first and second plate members in the first articulation position; and moving the first and second plate members into the one or more second articulation positions such that the ball element cannot be removed from the socket element, wherein the one piece socket element comprises an inner surface defining a recess sized and shaped to receive a substantial portion of the ball element and terminating at a peripheral edge such that one or more portions of the peripheral edge define one or more stand offs that form the one or more keyed surfaces for the one-piece socket element, the stand offs extend longitudinally away from the recess and beyond a transverse plane comprising the peripheral edge.

32. The method of claim 31, wherein the insertion step is carried out prior to implantation of the intervertebral disc replacement device into a patient.

33. The method of claim 31, wherein the insertion step is carried out during implantation of the intervertebral disc replacement device into a patient.

34. The method of claim 31, wherein the one or more first articulation positions are at least unlikely to be repeated after the intervertebral disc replacement device has been implanted in a patient.

35. The method of claim 31, wherein the one or more first articulation positions are not repeatable after the intervertebral disc replacement device has been implanted in a patient.

* * * * *